US00PP22408P2

(12) United States Plant Patent
Eveleens

(10) Patent No.: US PP22,408 P2
(45) Date of Patent: Dec. 27, 2011

(54) CARNATION PLANT NAMED 'HILREAL'

(50) Latin Name: *Dianthus caryophyllus*
Varietal Denomination: Hilreal

(75) Inventor: Peter Eveleens, Aalsmeer (NL)

(73) Assignee: Hilverda Kooij B.V., DeKwakel (NL)

( * ) Notice: Subject to any disclaimer, the term of this patent is extended or adjusted under 35 U.S.C. 154(b) by 0 days.

(21) Appl. No.: 12/924,020

(22) Filed: Sep. 17, 2010

(51) Int. Cl.
*A01H 5/00* (2006.01)

(52) U.S. Cl. ..... Plt./283

(58) Field of Classification Search ..... Plt./283
See application file for complete search history.

*Primary Examiner* — Annette Para
(74) *Attorney, Agent, or Firm* — C. A. Whealy

(57) ABSTRACT

A new and distinct cultivar of Carnation plant named 'Hilreal', characterized by its compact, upright, somewhat outwardly spreading, uniform and mounded plant habit; freely branching habit; freely flowering habit; large double red-colored flowers that are positioned above and beyond the foliar plane on strong peduncles; and good garden performance.

1 Drawing Sheet

Botanical designation: *Dianthus caryophyllus.*
Cultivar denomination: 'HILREAL'.

BACKGROUND OF THE INVENTION

The present invention relates to a new and distinct cultivar of Carnation plant, botanically known as *Dianthus caryophyllus,* grown commercially as a potted plant and hereinafter referred to by the name 'Hilreal'.

The new Carnation plant is a naturally-occurring whole plant mutation of *Dianthus caryophyllus* 'Allura', disclosed in U.S. Plant Pat. No. 20,079. The new Carnation plant was discovered and selected by the Inventor as a single flowering plant within a population of plants of 'Allura' in a controlled greenhouse environment in Aalsmeer, The Netherlands in June, 2005.

Asexual reproduction of the new Carnation plant by terminal cuttings propagated in a controlled greenhouse environment in Aalsmeer, The Netherlands since 2005, has shown that the unique features of this new Carnation plant are stable and reproduced true to type in successive generations of asexual reproduction.

SUMMARY OF THE INVENTION

Plants of the new Carnation have not been observed under all possible environmental conditions. The phenotype may vary somewhat with variations in environment such as temperature and light intensity, without, however, any variance in genotype.

The following traits have been repeatedly observed and are determined to be the unique characteristics of 'Hilreal'. These characteristics in combination distinguish 'Hilreal' as a new and distinct cultivar of Carnation plant:

1. Compact, upright, somewhat outwardly spreading, uniform and mounded plant habit.
2. Freely branching habit.
3. Freely flowering habit.
4. Large double red-colored flowers that are positioned above and beyond the foliar plane on strong peduncles.
5. Good garden performance.

Plants of the new Carnation differ from plants of the parent, 'Allura', in the following characteristics:

1. Leaves of plants of the new Carnation are not as waxy as leaves of plants of 'Allura'.
2. Plants of the new Carnation and 'Allura' differ in flower color as plants of 'Allura' have red purple-colored flowers.

Plants of the new Carnation can be compared to plants of the Carnation 'Napoli', not patented. In side-by-side comparisons conducted in Aalsmeer, The Netherlands, plants of the new Carnation differed from plants of 'Napoli' in the following characteristics:

1. Leaves of plants of the new Carnation were not as waxy as leaves of plants of 'Napoli'.
2. Plants of the new Carnation were more freely flowering than plants of 'Napoli'.
3. Plants of the new Carnation had larger flowers than plants of 'Napoli'.
4. Flower petals of plants of the new Carnation were more emarginate than flower petals of plants of 'Napoli'.
5. Flowers of plants of the new Carnation were darker red in color than flowers of plants of 'Napoli'.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant. The photograph comprises a side perspective view of a typical flowering plant of 'Hilreal' grown in a container.

DETAILED BOTANICAL DESCRIPTION

Plants used in the aforementioned photograph and following observations and measurements describe plants grown during the summer in 10.5-cm containers in a glass-covered greenhouse in Aalsmeer, The Netherlands and under conditions and practices which approximate those generally used in commercial potted Carnation production. During the production of the plants, day temperatures ranged from 20° C. to 25° C. and night temperatures ranged from 16° C. to 22° C. Plants were pinched one time four weeks after planting. Plants were three months old when the photograph and the detailed description were taken. In the following description, color references are made to The Royal Horticultural Society Colour Chart, 2007 Edition, except where general terms of ordinary dictionary significance are used.

Botanical classification: *Dianthus caryophyllus 'Hilreal'*.

Parentage: Naturally-occurring whole plant mutation of *Dianthus caryophyllus* 'Allura', disclosed in U.S. Plant Pat. No. 20,079.

Propagation:

*Type.*—By terminal cuttings.

*Time to initiate roots, summer.*—About six days at 20° C. to 25° C.

*Time to initiate roots, winter.*—About eight days at 18° C.

*Time to produce a rooted young plant, summer.*—About three weeks at 20° C. to 25° C.

*Time to produce a rooted young plant, winter.*—About five weeks at 18° C.

*Root description.*—Medium in thickness, fibrous; white in color.

*Rooting habit.*—Moderate branching; medium in density.

Plant description:

*Plant form.*—Compact, upright, somewhat outwardly spreading and mounded plant habit; narrow inverted triangle.

*Branching habit.*—Freely-branching growth habit; when pinched, about twelve lateral branches develop; dense and bushy growth habit.

*Plant height.*—About 16.2 cm.

*Plant diameter or spread.*—About 17.8 cm.

*Lateral branches.*—Length: About 6 cm. Diameter: About 3 mm. Internode length: About 2.2 cm. Strength: Strong. Texture: Smooth, glabrous. Color: Close to N137B.

Foliage description:

*Arrangement.*—Opposite, simple; sessile.

*Length.*—About 7 cm.

*Width.*—About 8 mm.

*Shape.*—Narrowly oblanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper and lower surfaces: Close to 143C; towards the base, close to 144C. Fully expanded leaves, upper surface: Close to 136A and 137A; venation, close to 136A and 137A. Fully expanded leaves, lower surface: Close to 137A to 137B; ventation, close to 143A.

Flower description:

*Flower type and habit.*—Large double flowers; flowers terminal and axillary, either solitary or in pairs; freely flowering habit with typically about 48 flowers developing per plant; flowers positioned above and beyond the foliar plane on strong peduncles; flowers face mostly upright.

*Fragrance.*—Flowers faintly fragrant; sweet, clove-like.

*Natural flowering season.*—Flowering is continuous through the summer and late summer in The Netherlands; plants begin flowering about 13 weeks after planting.

*Flower longevity.*—Flowers last about ten days on the plant; flowers not persistent.

*Flower diameter.*—About 4.8 cm.

*Flower depth.*—About 3.9 cm.

*Flower buds.*—Length: About 1.6 cm. Diameter: About 1.6 cm. Shape: Elliptic. Color: Close to 143A to 143B slightly flushed with close to 165A.

*Petals/petaloids.*—Quantity/arrangement: About 40 per flower arranged in several whorls. Length, outer petals: About 4.2 cm. Width, outer petals: About 2.2 cm. Shape: Roughly spatulate. Apex: Praemorse. Base: Acute. Margin: Entire. Texture, upper and lower surfaces: Smooth, glabrous; velvety. Color: When opening, upper surface: Close to 51A; towards the base, close to 145D. When opening, lower surface: Close to 51B; towards the base, close to 145D. Fully opened, upper surface: Close to 46B to 46C and 47A; towards the base, close to 145D. Fully opened, lower surface: Close to 47A; towards the base, close to 145D.

*Sepals.*—Quantity/arrangement: Five fused in a single whorl. Length: About 2.2 cm. Width: About 7 mm. Shape: Oblong. Apex: Broadly acute. Margin: Entire. Texture, upper and lower surfaces: Smooth, glabrous. Color, upper surface: Close to 148C; apex heavily tinged with close to 181B to 181C. Color, lower surface: Close to 137A to 137B; apex heavily tinged with close to 200B.

*Peduncles.*—Length: About 6 mm. Diameter: About 2 mm. Strength: Strong. Texture: Smooth, glabrous. Color: Close to N137B.

*Reproductive organs.*—Stamens: None observed. Pistils: Quantity: About two per flower. Pistil length: About 2.5 cm. Stigma shape: Club-shaped. Stigma color: Close to 51A. Style length: About 2.4 cm. Style color: Close to 51B to 51D; towards the base, close to NN155C. Ovary color: Close to 145B to 145D. Fruits/seeds: Fruit and seed development have not been observed on plants of the new Carnation.

Disease/pest resistance: Plants of the new Carnation have not been observed to be resistant to pathogens and pests common to Carnations.

Garden performance: Plants of the new Carnation have been observed to have good garden performance and to tolerate wind, rain and temperatures ranging from about 5° C. to 35° C.

It is claimed:

1. A new and distinct Carnation plant named 'Hilreal' as illustrated and described.

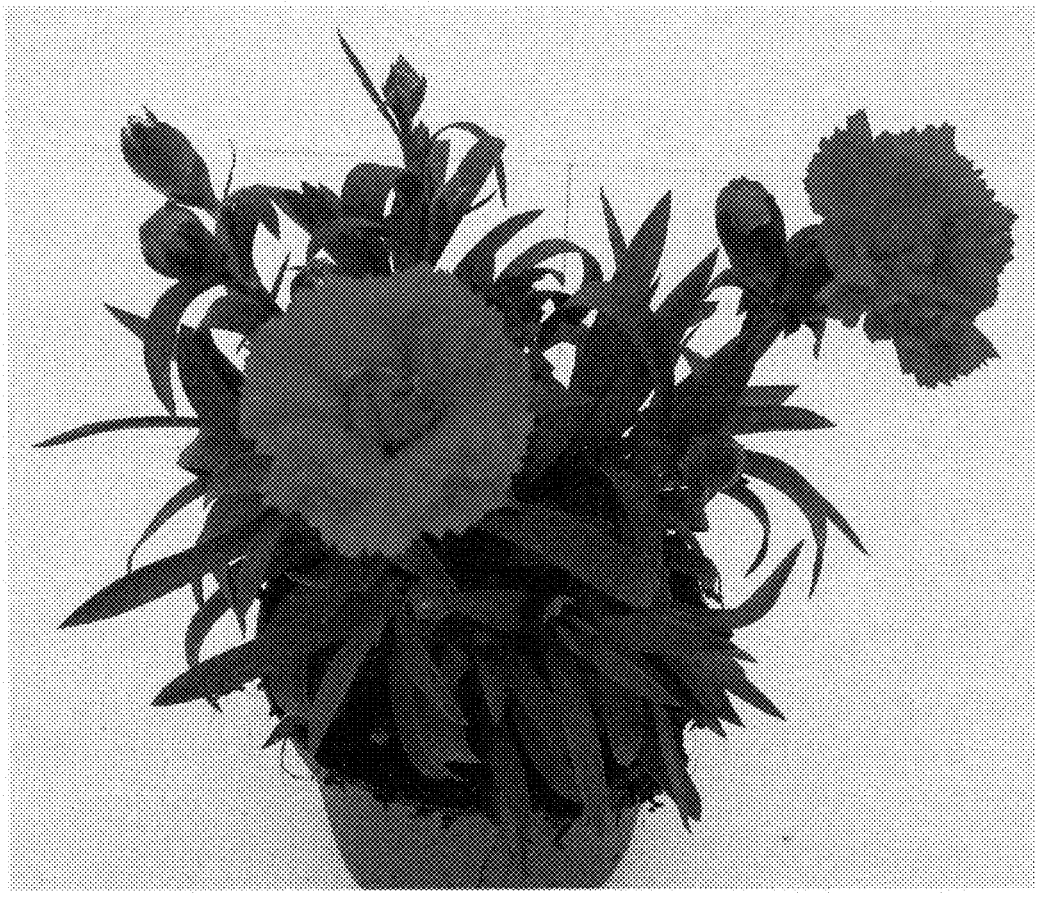

* * * * *